US009868677B2

(12) United States Patent
Diniz Campos et al.

(10) Patent No.: US 9,868,677 B2
(45) Date of Patent: Jan. 16, 2018

(54) PROCESS FOR OBTAINING A FORMULATION WITH FERTILIZING AND PHYTOPROTECTIVE CAPABILITY, A FORMULATION WITH FERTILIZING AND PHYTOPROTECTIVE CAPABILITY, USE OF A FORMULATION WITH FERTILIZING AND PHYTOPROTECTIVE CAPABILITY

(71) Applicants: EMPRESA BRASILEIRA DE PESQUISA AGROPECUARIA—EMBRAPA, Brasilia, DF (BR); Universidade Federal do Rio Grande do Sul, Porto Alegre, RS (BR)

(72) Inventors: Angela Diniz Campos, Pelotas (BR); César Bauer Gomes, Brasilia (BR); Fabiane Grecco Da Silva Porto, Capao do Leao (BR); Irene Teresinha Santos Garcia, Porto Alegre (BR); Irajá Ferreira Antunes, Pelotas (BR); Bernardo Ueno, Pelotas (BR); Luis Antônio Suita de Castro, Brasilia (BR); José Francisco Martins Ferreira, Brasilia (BR); Walkyria Bueno Scivittaro, Pelotas (BR)

(73) Assignees: EMPRESA BRASILEIRA DE PESQUISA AGROPECUARIA—EMBRAPA, Brasilia—DF (BR); Universidade Federal do Rio Grande do Sul, Porto Alegre, RS (BR)

( * ) Notice: Subject to any disclaimer, the term of this patent is extended or adjusted under 35 U.S.C. 154(b) by 0 days.

(21) Appl. No.: 14/655,953

(22) PCT Filed: Dec. 26, 2013

(86) PCT No.: PCT/BR2013/000597
§ 371 (c)(1),
(2) Date: Jun. 26, 2015

(87) PCT Pub. No.: WO2014/100873
PCT Pub. Date: Jul. 3, 2014

(65) Prior Publication Data
US 2015/0336854 A1 Nov. 26, 2015

(30) Foreign Application Priority Data
Dec. 26, 2012 (BR) .......................... 10 2012 0331497

(51) Int. Cl.
| | | |
|---|---|---|
| *A01N 61/00* | (2006.01) | |
| *A01N 43/16* | (2006.01) | |
| *A01N 63/02* | (2006.01) | |
| *C05G 3/02* | (2006.01) | |
| *A01N 61/02* | (2006.01) | |
| *C05D 3/00* | (2006.01) | |
| *C05D 9/02* | (2006.01) | |
| *C05F 1/00* | (2006.01) | |

(52) U.S. Cl.
CPC ............... *C05G 3/02* (2013.01); *A01N 61/00* (2013.01); *A01N 61/02* (2013.01); *C05D 3/00* (2013.01); *C05D 9/02* (2013.01); *C05F 1/005* (2013.01); *Y02P 20/145* (2015.11); *Y02W 30/43* (2015.05)

(58) Field of Classification Search
None
See application file for complete search history.

(56) References Cited

FOREIGN PATENT DOCUMENTS

| | | | |
|---|---|---|---|
| CN | 1690018 A | | 11/2005 |
| CN | 101691490 A | | 4/2010 |
| CN | 102988752 | * | 3/2013 |
| JP | 06065019 | * | 3/1994 |
| JP | 2000-053964 A | | 2/2000 |
| JP | 2002-053385 A | | 2/2002 |
| JP | 2009001522 | * | 1/2009 |
| JP | 2001335392 | * | 12/2011 |

OTHER PUBLICATIONS

International Preliminary Report on Patentability dated Jun. 30, 2015 from the International Bureau in counterpart International Application No. PCT/BR2013/000597.
International Search Report of PCT/BR2013/000597 dated Feb. 25, 2014.

* cited by examiner

*Primary Examiner* — Alton Pryor
(74) *Attorney, Agent, or Firm* — Sughrue Mion, PLLC

(57) ABSTRACT

The present invention falls into the context of green chemistry and generically relates to a fertilizing and phytoprotective formulation and, in particular embodiment, to a film forming formulation that induces resistance to plants.

The respective formulation, when applied to plants and/or fruits, results in the formation of a film on the surface of the material, which has a characteristic of photoprotection against UV-B and UV-C radiations, resistance kept in water, even after high hygroscopicity, greater stability at high ambient temperatures, formation of desired porosity and surface homogeneity.

17 Claims, 10 Drawing Sheets
(7 of 10 Drawing Sheet(s) Filed in Color)

A

B

PROCESS FOR OBTAINING A FORMULATION WITH FERTILIZING AND PHYTOPROTECTIVE CAPABILITY, A FORMULATION WITH FERTILIZING AND PHYTOPROTECTIVE CAPABILITY, USE OF A FORMULATION WITH FERTILIZING AND PHYTOPROTECTIVE CAPABILITY

CROSS REFERENCE TO RELATED APPLICATIONS

This is a National Stage of International Application No. PCT/BR2013/000597 filed Dec. 26, 2013, claiming priority based on Brazilian Patent Application No. 10 2012 0331497 filed Dec. 26, 2012, the contents of all of which are incorporated herein by reference in their entirety.

FIELD OF THE INVENTION

The present invention falls into the context of green chemistry and generically relates to a fertilizing and phytoprotective formulation and, in particular embodiment, to a film forming formulation that induces resistance to plants.

DESCRIPTION OF THE PRIOR ART

Within the concept of sustainability, environmental chemistry and/or green chemistry has advanced toward introducing processes and products for replacement of polluting technologies. The use of raw-materials of vegetable origin and/or byproducts resulting from the processing of said raw-materials and the incorporation thereof into ecologically correct processes/products has proved to be a worldwide tendency, chiefly in countries that have great availability of biomass.

All over the world, the production of charcoal by burning wood is viewed as an unhealthy and highly polluting activity, chiefly because of the launching of toxic substances into the environment. In this context, the reduction of this launching as well as the use of the by-products of the process in agriculture is viewed as an environmentally correct and economically feasible solution to the sector.

During the wood-carbonizing process, charcoal is only a fraction of the products that can be obtained. If one uses appropriate systems for collection, one will take advantage of pyroligneous condensates (pyroligneous fraction or pyroligneous liquid) and the non-condensable gases. The more complete and efficient practice is the utilization of charcoal, condensates and also non-condensable gases from wood by the "dry-distillation" process. The best known liquid phase, which may be used in agriculture, is the pyroligneous liquid, called pyroligneous extract, pyroligneous acid, wood vinegar, pyrolignous liquor, liquid smoke or bio-oil. Wood carbonization is the main source of this substance. At present, the main pyroligneous-extract producing countries are Japan, China, Indonesia, Malasya, Brazil and Chile, including other countries of Southeast Asia and South Africa. The manufacture and use of pyroligneous extract is very ancient. In China there are reports about the use thereof thousands of years ago and in India it is much used in the treatment of diseases.

In order to produce pyroligneous extract, it is necessary to condensate the vapors contained in the smoke, thus obtaining liquor composed basically by tar, pyroligneous acid and vegetable oils, which can be separated by decantation or by a distillation process. Pyroligneous acid or pure pyroligneous extract enhance the positive aspects and inhibits the negative ones in agricultural production at the same time. The gases that emanate from furnaces are canalized and, after formation of the liquor, decantation takes place in barrels. The pyroligneous extract obtained functions as both pest controller and organic manure. Another advantage of the product is that, since it exhibits low pH, it acts as a catalyst of acidic chemical defensives when mixed with them, and can reduce the volume of these products without detriment to the efficiency.

After its extraction, the pyroligneous extract is kept at rest for 3 to 6 months until its reactions cease and its components are stabilized. The elimination of tar and other impurities from the pyroligneous extract should be made by leaving the liquid at rest for up to 6 months, so that decantation of the impurities takes place. After this period, the liquid will be separated into three different layers. In the first layer there is predominance of vegetable oils, in the second layer there is predominance of pyroligneous extract and in the third layer there is predominance of tar. After separation by decantation, the extract obtained is called crude pyroligneous extract (CPE) and, according to the necessary application, may be filtered or distilled.

Various formulations comprising CPE are described in the literature, being used chiefly as agricultural fertilizers and plant resistance activator. Among these formulations one can cite that described in document JP 6056617, which describes a composition applied to the soil, fish and plants and which promotes the improvement of the immunological activity, improvement in the physiological function and has antimicrobial function. The respective formulation comprises distilled pyroligneous extract (800 L), mixed with aqueous solution containing dextrin, chitin, chitosan (3 kg-8 kg), a soluble garlic component, 300 ppm of aqueous organic germanium solution and 3%-8% aqueous acetic-acid solution. Document JP 6287104 describes a vegetable activator comprising pre-treated wood vinegar and chitosan. The pre-treatment of wood vinegar consists in mixing it with 1.5 to 3.0 equivalents of $HSO_3^{-1}$ or hydrazines to inactivate 1 equivalent of aldehydes. The wood vinegar thus treated is then mixed with chitosan in the ratio of 98.5-30%:5-1.5% (m %). Document KR 20080074258 presents an antimicrobial composition comprising silver nanoparticle, chitosan and pyroligneous liquor. More specifically, the composition comprises 1.0-5.0% of chitosan solution, 1.0%-2.0% of pyroligneous liquor and 1000 ppm-5000 ppm of silver. Document JP 6197630 describes a method for growing mushroom, which comprises adding a plant growth agent containing diluted chitosan solution and wood vinegar diluted in water. Said method controls the occurrence of various microorganisms, promotes the growth of mushrooms, improves the harvest, reduces the cultivation period and results in high-quality mushrooms.

As can be seen from the analysis of the documents cited before, formulations comprising pyroligneous extract for agricultural application have, as one of their components, chitosan, which usually acts to enable the formation of films on the treated agricultural material. The employ of chitosan is also described with the same function in various other documents, like JP200334211, KR 979931 and KR 20110094370. Although widely employed, these formulations for application in agriculture comprising chitosan and pyroligneous extract, exhibit, after application, limiting characteristics, such as low stability of the film, irregularity thereof and quite heterogeneous fibrous structure of the material. These characteristics result in films with lower resistance, shorter durability and formulations of little applicability in the field.

Within this context, the present invention relates to a process for obtaining a formulation, as well as a formulation with phytoprotective and fertilizing characteristics, and which represents a feasible alternative of composition for application on plants and fruits. The respective formulation has the differential of keeping its characteristics after application by forming a stable film, with longer durability, thermal resistance, and better resistance upon absorbing water, thus being ideal for application in the field. These characteristics are achievable by employing a combination of specific components in predetermined concentrations, which guarantee the characteristics cited herein. Among the characteristics of the formulation of the invention and, as a result, of the product formed after application to plant and fruits, one can cite the induction of systemic resistance, proven fugitoxic and nematicidal action, formation of film on the plant surface after the formulation is sprayed, photoprotection against UV-B and UV-C radiations, resistance of the film is kept in water, even after absorption, greater stability of the film at high ambient temperatures, desired formation of porosity, and homogeneity of photoprotective surface.

SUMMARY OF THE INVENTION

The present invention presents a process for obtaining a formulation with fertilizing and phytoprotective capability, such process comprising the following steps:
A) obtaining distilled pyroligneous extract (DPE);
B) obtaining a composition comprising DPE and chitosan;
C) obtaining a fertilizing mineral solution;
D) mixing the composition obtained in step B with the solution obtained in step C.

The invention also relates to a formulation with fertilizing and phytoprotective capability, this formulation comprising distilled pyroligneous extract (DPE), chitosan and minerals.

The invention further relates to the use of a formulation with fertilizing and protective capability of the invention in application to plants, parts of plants, including fruits.

The patent of application file contains at least one drawing executed in color. Copies of this patent or patent application publication with color drawing(s) will be provided by the office upon request and payment of the necessary fee.

DETAILED DESCRIPTION OF THE INVENTION

Figure 1:
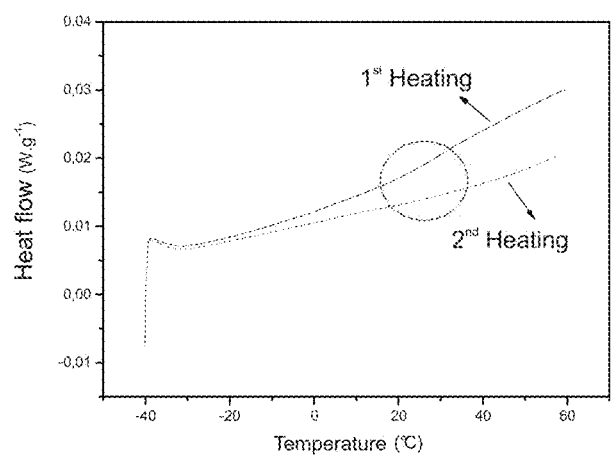
FIG. 1—Thermograms obtained through differential scanning calorimetry of chitosan on distilled pyroligneous acid, with heating rate of 10° C. min-1.

The present invention relates to a process for obtaining a formulation, as well as to a formulation with phytoprotective and fertilizing characteristic and which represents a feasible alternative composition for application to plants and fruits, while keeping it characteristics by forming a stable film, with greater durability, thermal resistance and keeping the characteristics upon absorption of water, being ideal for field application.

Said invention uses a by-product of the process for obtaining charcoal from the burning of wood for, after a specific treatment, using it in combination with chitosan and specific minerals, thus obtaining a formuation that, after application to plants, has desirable characteristics and so far not fully achieved by similar products, such as induction of the systemic resistance, proven fungitoxic and nematicidal action, formation of a film on the plant surface after being sprayed, photoprotection against UV-B and UV-C radiations, resistance of the film being kept in water even after high absorption, greater stability of the film at high ambient temperature, formation of desired porosity and homogeneity of photoprotective surface.

After application to plants and fruits, the film formed efficiently blocks the radiation in the UV-B and UV-C regions. The high molar absorptivity decreases with the increase in wavelength. The formulation is thermally stable up to 60° C. and the resulting film loses a small amount of water under heating, but is thermally stable at a wide temperature range, undergoing decomposition only at 300° C. The film exhibits semi-crystalline structure, which imparts to it flexibility and porosity, which are desirable characteristics in the water-penetration and gas-exchange processes.

The film maintains its integrity under immersion in water for up to 7 days and exhibits excellent hygroscopicity, and can absorb water up to 300% of its mass with little loss of the initial characteristics, which enables the use thereof as coverings for plants in ambient conditions.

The invention relates to a process for obtaining a formulation with fertilizing and phytoprotective capability. The invention also deals with the formulation with fertilizing and phytoprotective capability. The respective formulation promotes the formation of a film capable of coating the surface where it is applied, be it a plant or a fruit. The film produced from this formulation keeps stability in water for up to one week, efficiently blocks UV-B and UV-C radiation, is thermally stable up to 60° C. and has semi-crystalline structure, which imparts to it flexibility and porosity, which are desirable characteristics in the water-penetration and gas-exchange processes carried out by the plants. The formulation of the present invention exhibits fungitoxic action in vitro for *Monilinia fructicola* and *Colletotrichum*, and nematicidal action on second-stage juveniles of *M. graninicola* and *M. javanica*, with in vitro mortality. The formulation also stimulates the enzymes related to the environmental defense and stress mechanisms of the plants (peroxidase (PO), phenylalaninammonia-liase (FAL), β1,3 glucanase (β 1,3)). Said formulation partially inhibits the natural senescence process of the fruit coming from plants treated with promotion of total or partial healing of the wounds. It further acts by decelerating the hydrolysis process of pectin in stored apples, keeping the pectin contents for a longer period of time, and natural juiciness in apples, imparting greater quality to the fruits in pre-harvest applications.

The process for obtaining the formulation with fertilizing and phytoprotective capability of the present invention comprises the following steps:
  A) Obtaining distilled pyroligneous extract (DPE);
  B) Obtaining a composition comprising DPE and chitosan;
  C) Obtaining a fertilizing mineral solution;
  D) Mixing the composition obtained in step B with the solution obtained in step C.

In the present invention, the distilled pyroligneous extract (DPE) is obtained from crude pyroligneous extract (CPE). By "crude pyroligneous extract" one understands the liquid phase obtained upon condensation of smoke during the burning of the wood for the production of charcoal. The CPE is also called pyroligneous liquid or pyroligneous acid or wood vinegar or pyroligneous liquor or liquid smoke or bio-oil. In the case of the CPE of the present invention, it should be produced by using control parameters that enable one to obtain a product with the smallest amount of tar possible. The presence of tar in the CPE makes it toxic and unfeasible for use in agriculture. In the case of the present invention, the CPE is obtained according to the obtainment guidelines described in Campos, A. D. (*Técnicas de produção de extrato pirolenhoso para use agricola. Embrapa Clime Temperado, Circular Técnica* no. 65, 2007. ISSN 1981-5999). As part of the process of obtaining/separating, the CPE is kept at rest for 3 to 6 months and separated by decantation from the other components resulting from the condensation of smoke. Alternatively, after separation thereof from the other components resulting from the condensation of smoke, the CPE obtained may further be subjected to a filtration process with a view to eliminate remaining impurities. In the present invention, the EPD is obtained from vacuum distillation of the CPE. More specifically, the EPD is obtained from vacuum distillation at minimum and maximum temperatures of 60° and 75° C., respectively.

Step B of the process for obtaining a fertilizing and phytoprotective formulation of the present invention comprises obtaining a precursor composition containing DPE and chitosan. In order to obtain the respective precursor composition, chitosan is mixed with the DPE. Preferable, for use thereof in the present invention, chitosan should have a minimum degree of deacetylation, of 97%. Further preferably, the concentration of chitosan ion DPE in the composition obtained in step B of the invention should range from 0.05 g/L to 30 g/L, resulting in a conductivity of the composition obtained in B that should range from 1038 µS $cm^{-1}$ to 4970 µS $cm^{-1}$. In a preferred embodiment, the concentration of chitosan in DPE in the composition obtained ion step B of the process is of 10 g/L, resulting in a conductivity of 1938 µS $cm^{-1}$ to 2190 $cm^{-1}$.

The obtention of the fertilizing mineral solution described in step C of the process for obtaining the fertilizing and phytoprotective formulation of the present invention is carried out by adding minerals to the water. Various minerals with fertilizing capability may be used in obtaining the mineral solution (step C) of the present invention. Preferably, the minerals are selected from silicon and/or boron and/or molybdenum and/or manganese and/or zinc and/or calcium and/or copper. Further preferably, the concentrations of the respective minerals used are: silicon: 0.07 g/L to 0.50 g/L; boron: 0.04 g/L to 0.08 g/L; molybdenum: 0.02 g/L to 0.09 g/L; manganese: 0.04 g/L to 0.13 g/L; zinc: 0.02 g/L to 0.10 g/L; calcium; 0.03 g/L to 0.30 g/L; copper 0.065 g/L to 0.2 g/L.

Step D of the process for obtaining the fertilizing and phytoprotective formulation of the present invention comprises mixing the composition obtained in step B with the solution obtained in step C of the process. Preferably, the mixture ratio between the solutions B:C ranges from 0.05:99.95 to 30:70. The mixture of the solutions B and C at the ratios described before results then in the fertilizing and phytoprotective formulation of the invention.

The present invention also relates to a formulation with fertilizing and phytoprotective capability, comprising such formulation, DPE, chitosan and minerals. More specifically, the invention relates to a fertilizing and phytoprotective formulation comprising DPE, chitosan and minerals, where preferably the concentration of chitosan in the formulation ranges from $2.5 \times 10^{-5}$ g/L to 9 g/L. Various minerals having fertilizing function may be present in the formulation of the invention. Preferably, the minerals present in the fertilizing and phytoprotective formulation of the invention are selected from silicon and/or boron and/or molybdenum and/or manganese and/or zinc and/or calcium and/or copper, which, when present, exhibit the following concentrations: silicon: 0.049 g/L to 0.5 g/L; boron: 0.028 g/L to 0.08 g/L; molybdenum: 0.014 g/L to 0.09 g/L; manganese: 0.028 g/L to 0.13 g/L; zinc: 0.014 g/L to 0.1 g/L; calcium: 0.021 g/L to 0.3 g/L; copper 0.046 g/L to 0.2 g/L.

The present invention further relates to a formulation with fertilizing and phytoprotective capability comprising distilled pyroligneous extract (DPE), chitosan and minerals and obtained according to the formulation obtainment process described in this document. More specifically, the invention relates to a fertilizing and phytoprotective formulation comprising DPE, chitosan and minerals, obtained according to the formulation obtainment process described in this document, where preferably the concentration of chitosan in the formulation ranges from $2.5 \times 10^{-5}$ g/L to 9 g/L. Various minerals with fertilizing function may be present in the formulation obtained according to the process described in this document. Preferably, the minerals present in the formulation are selected from silicon and/or boron and/or molybdenum and/or manganese and/or zinc and/or calcium and/or copper, which, when present, exhibit the following concentrations: silicon: 0.049 g/L to 0.5 g/L; boron: 0.28 g/L to 0.08 g/L; molybdenum: 0.014 g/L to 0.09 g/L; manganese: 0.028 g/L to 0.13 g/L; zinc: 0.014 g/L to 0.1 g/L; calcium; 0.021 g/L to 0.3 g/L; copper 0.046 g/L to 0.2 g/L.

The present invention further relates to the use of a formulation with fertilizing and phytoprotective capability as described before, for application to plants, parts of plants, including fruits. More specifically, the invention relates to the use of the respective formulation described in the invention for obtaining a film on plants and/or fruits, which has phytoprotective and fertilizing characteristic.

EXPERIMENTAL RESULTS

Physicochemical Characterization of the Composition Obtained in Step B of the Process for Obtaining a Fertilizing and Phytoprotective Formulation The compositions of chitosan in distilled pyroligneous acid were characterized as to the presence of electrolytes in solution through measurements of pH and conductivity, which were carried out on Digimed equipment, models DM-20 and DM-31, respectively.

The conductivity and the pH of the solutions of chitosan in distilled pyroligneous acid, at different concentrations, are shown in Table 1. The determination of the conductivity is important to characterize the presence of electrolytes in solution, since it has direct influence on the formation of gel and on the polymer hydration radius. The pH is important, since studies suggest that chitosan has greater antifungal potential at acidic pH in the range 3 to 4.

TABLE 1

Physicochemical characteristics of the solutions of chitosan in distilled pyroligneous acid

| Concentration (g L$^{-1}$) | Conductivity (µS cm$^{-1}$) | pH |
|---|---|---|
| 0 | 1035 | 3.26 |
| 0.05 | 1038 | 2.95 |
| 0.1 | 1035 | n.d. |
| 0.5 | 967 | 2.91 |
| 1.0 | 991 | 2.95 |
| 2.0 | n.d. | 3.06 |
| 2.5 | 1101 | n.d. |
| 5.0 | 1410 | n.d. |
| 10.0 | 2180 | 3.23 |
| 15.0 | n.d. | 2600 |
| 30.0 | 3.43 | 4970 |

The thermal behavior of gels was determined through differential scanning calorimetry (DSC). The DSC measurements were carried out on a DSC Q 20 from TA Instruments, at a temperature interval of −40° C. to 60° C., with heating rate of 10° C.min$^{-1}$ under nitrogen flow of 50 mL·min$^{-1}$.

FIG. 1 shows the thermal behavior of the gel formed by the chitosan/distilled pyroligneous acid system. The DSC analysis was carried out with two heating cycles and one cooling cycle. One carried out consecutive heating ramps.

One observes in FIG. 1 a discontinuity at approximately 24° C. in the curve of the 1° heating, which does not repeat in the 2° heating, which suggests only a loss of water by the gel in the first heating. It was not possible to observe any phase transition showing that the gel remained stable in the temperature range studied.

Characterization of the Films
Capability of Blocking the UV/VIS Radiation

Figure 2:
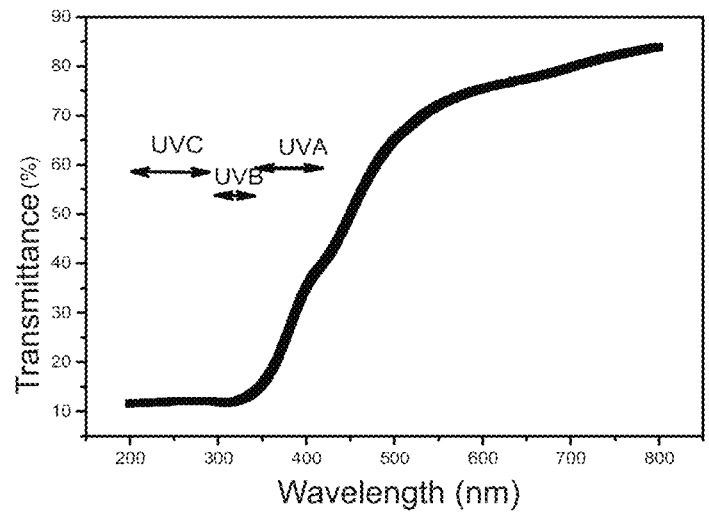
FIG. 2—A) Transmittance as a function of the wavelength of chitosan/distilled pyroligneous acid films with thickness of 50 µm; B) Molar absorptivity of chitosan/distilled pyroligneous films as a function of the wavelength.
Figure 2:
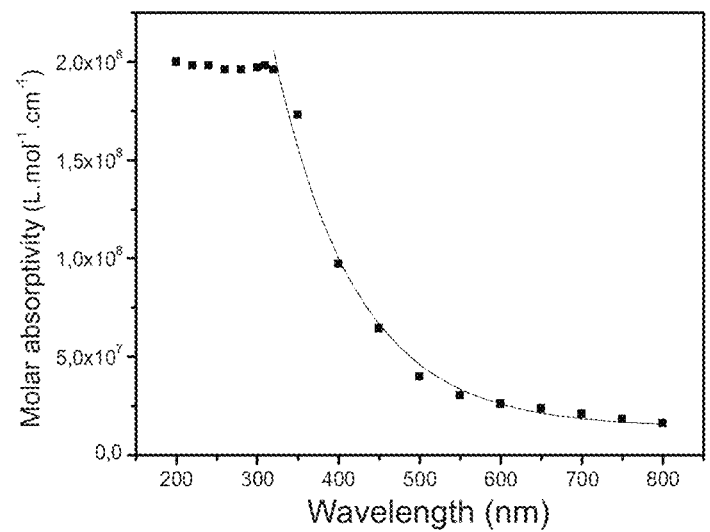

The typical behavior of UV/VIS transmittance of chitosan/distilled pyroligneous acid films is shown in FIG. 2-A. The transmittance of the films was evaluated at a thickness interval that obeys the Lambert-Beer Law. The molar absorptivity was calculated for different wavelengths through the expression of Lambert-Beer (1) described below:

$$A(\lambda)=\epsilon(\lambda)bc \quad (1),$$

wherein A is the absorbance of the films, $\epsilon$ is the is the molar absorbance, b is the film thickness and c is the concentration.

Considering the thickness of the films and the concentration, one calculated the partial molar absorptivities that were expressed as a function of the wavelength in FIG. 2-B. The results for the molar absorptivity as a function of the wavelength after 320 ηm were obtained through the equation (2) described below:

$$y=4.6.109e(-x/100)+1.4.107 \quad (2).$$

The spectral range covered showed that these films can be used as photoprotectors, blocking almost completely the UV-B (310-280 ηm) and UV-C (279-200 ηm) radiations.

Structural Characteristics of the Films

Figure 3:
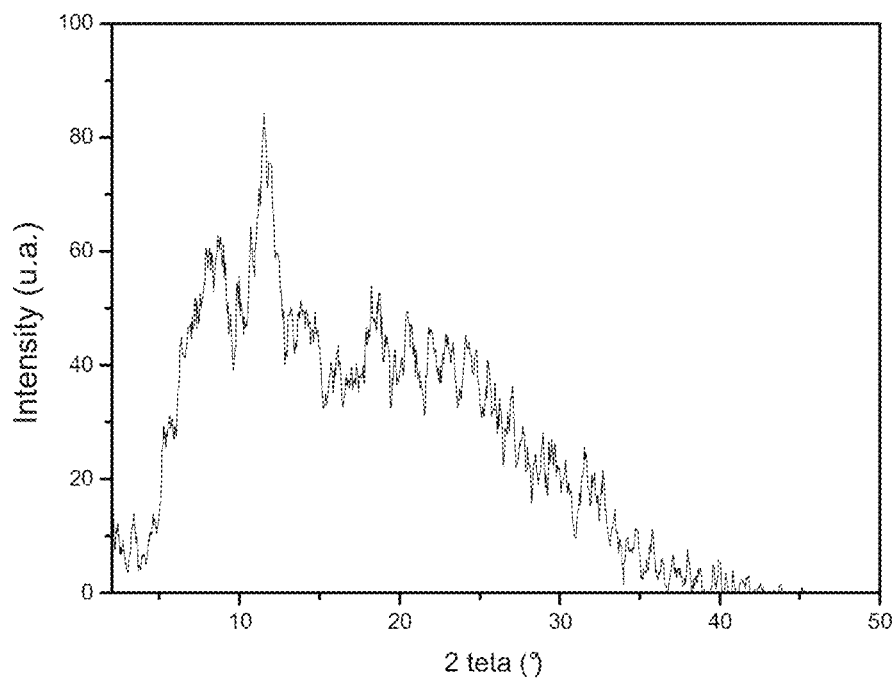
FIG. 3—X-ray diffraction spectrum of the chitosan/distilled pyroligneous acid film, $\lambda=0.1542$ ηm.

The X-ray diagram of the films (FIG. 3) showed the peaks at 2θ, 8.4-8.6 and 11.55°, located over a huge halo characteristic of amorphous materials. The films then exhibited a semi-crystalline structure. This semi-crystalline characteristic is interesting, since it provides the film with flexibility and porosity, which are desirable characteristics in the water-penetration and gas-exchange processes.

Thermal Stability

Figure 4:
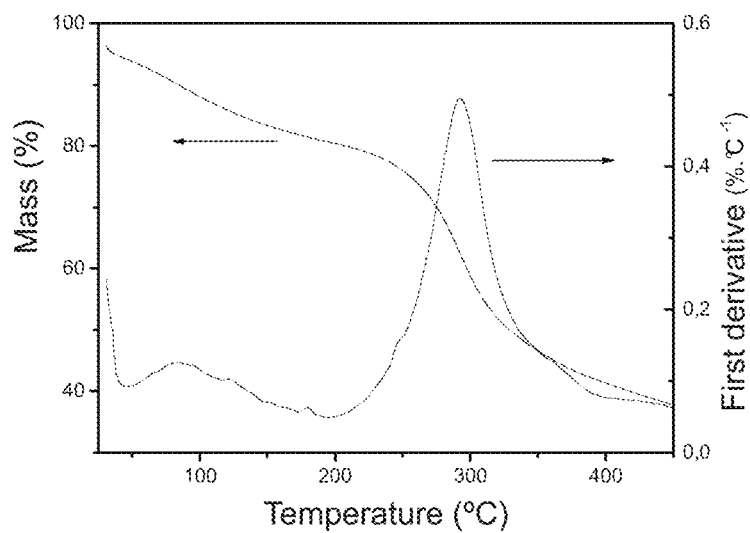
FIG. 4—Thermogravimetric analysis profile, and first derivative of the chitosan/distilled pyroligneous acid films.

The profiles of the thermogravimetric analysis and of the first derivative of the chitosan/distilled pyroligneous acid films are shown in FIG. 4. At 45° C., the films lost about 20% of mass, which is attributed to the release of water and acetic acid caught in their structure. At 300° C., chitosan began to degrade. The remaining material (about 40% by mass) exhibited characteristics of amorphous carbon.

Behavior of the Films in Water

The films proved to be stable in water, without undergoing disintegration for up to one weak of immersion. The hygroscopic characteristic of the film was determined by varying the mass of water absorbed by the films according to the equation (3):

$$\Delta m = \left(\frac{m_i - m_0}{m_0}\right) * 100, \quad (3)$$

wherein $\Delta m$ is the relative increase in mass, $m_0$ is the initial mass of the film and $m_i$ is the mass of the film in the immersion time i.

Figure 5:
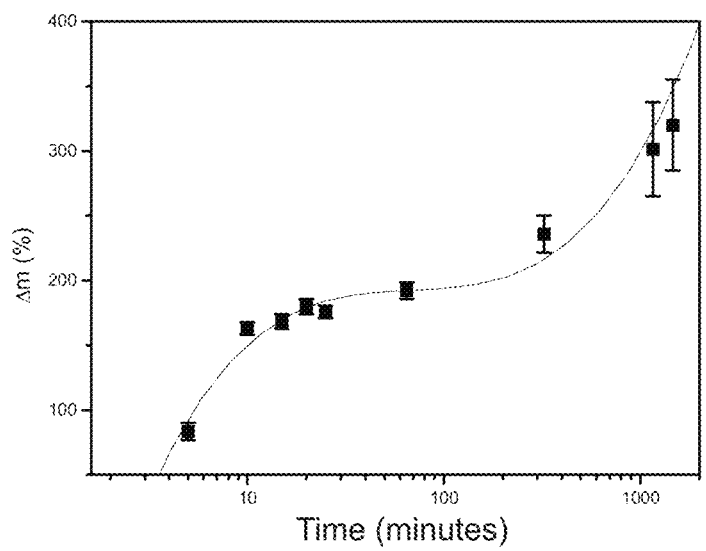
FIG. 5—Relative mass variation of the chitosan/distilled pyroligneous acid films after different times of immersion in distilled water at 25° C.

FIG. 5 shows the increase in water absorption of the films as a function of the time. The film came to the point of increasing by 300% its mass in water.

Figure 6:
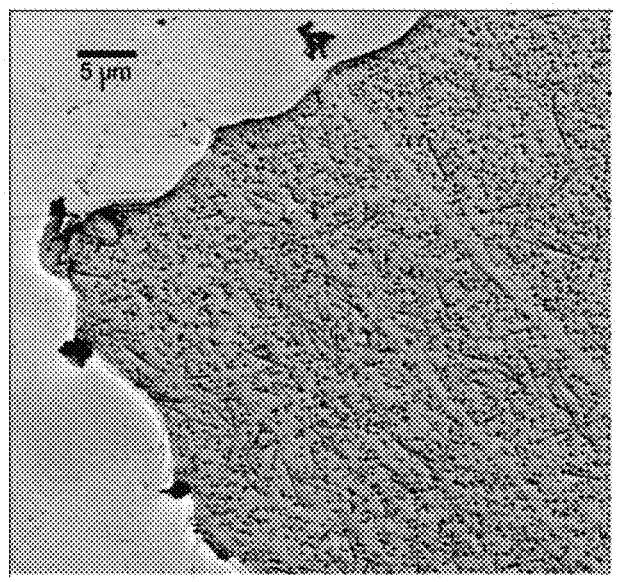
FIG. 6—Electronic micrography of the chitosan/distilled pyroligneous acid film after spraying on a smooth surface at a temperature ranging from 18 to 25° C.
Figure 7:
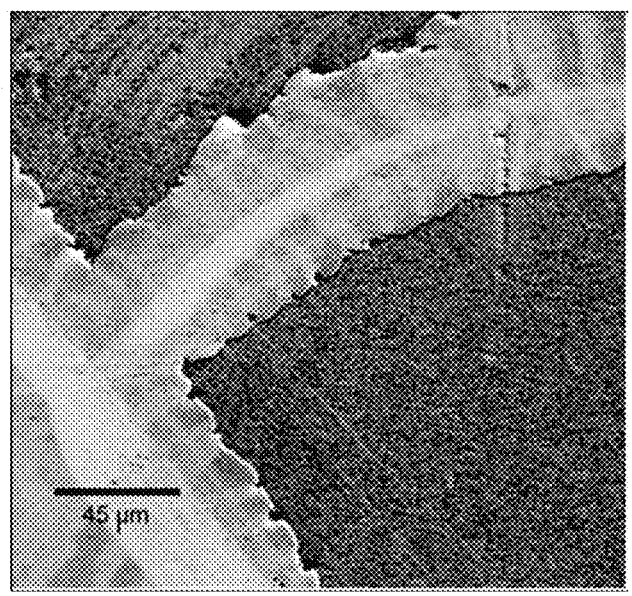
FIG. 7—Electronic micrography of the chitosan/distilled pyroligneous acid film after spraying on a smooth surface at a temperature ranging from 18 to 25° C.

FIGS. 6 and 7 show electronic micrographies of the chitosan/distilled pyroligneous acid film, after spraying on a smooth surface at a temperature ranging from 18 to 25° C.

Behavior of the Plant after Treatment

Figure 8A:
FIG. 8—A partial view of the experiments for evaluation of the efficiency of the formulates in reducing the incidence of anthracnose on beans plant, (A) plants in wet chambers after inoculation of *Colletotrichum lindemuthianum* spores, (B) plants before inoculation of the fungus.
Figure 8B:

The phytoprotective and fertilizing formulation of the invention promotes an increase in the adhesion of the molecules to the plant cuticle, enabling better contact between the formulation of the invention, nutrient and the leaf surface. In FIGS. 8A and 8B, one shows partial views of the experiments for evaluation of the efficiency of the formulations in reducing the incidence of anthracnose on beans plant. In FIG. 8A, one shows plants in wet chambers after inoculation of *Colletotrichum lindemuthianum* spores, and in FIG. 8B one shows the plants before inoculation of the fungus.

Table 2 below shows the disease index according to McKINNEY for incidence of anthracnose after application of the phytoprotective and fertilizing formulation of the invention.

TABLE 2 disease index according to McKINNEY for incidence of anthracnose

| Cultivars | Chocolate | | "Macanudo" | |
|---|---|---|---|---|
| Treatments | Exp. III* | Exp. IV* | Exp. III | Exp. IV |
| Formulation A | 0.97 | 0.47 | 0.33 | 0.20 |
| Pyroligneous acid/chitozan/minerals | 0.96 | 0.43 | 0.20 | 0.13 |
| Pyroligneous acid/chitosan | 0.99 | 0.33 | 0.29 | 0.17 |
| T1a-Test. with inoculum | 1 | 0.88 | 0.37 | 0.24 |
| T1b-Test. with inoculum and with fungicide | 0.20 | 0.11 | 0.11 | 0.11 |

*Experiment III—one application
*Experiment IV—three applications, except for witnesses One can observe in Table 2 that, after three applications of the formulations, the responses of the plants were significant as to the resistance to anthracnose (*Colletotrichum lindemuthianum*). The Mackinney index equal to 1 corresponds to the high incidence of disease and high susceptibility to anthracnose. After three applications of the formulation of the invention, one found that the Mckinney index came down to less than 0.50, which means that plants that were susceptible before, had now intermediate resistance. The cultivar Macanudo, considered susceptible to anthracnose, became resistant, exhibiting a Mckinney index of 0.33 (DPE+chitosan) and 0.43 (DPE+chitosan+minerals). The cultivar chocolate exhibited, after 3 applications, Mckinney indexes of 0.17 (DPE+chitosan) and 0.13 (DPE+chitosan+minerals), respectively.

Figure 9:
FIG. 9—Evaluation of the effect of the phytoprotector of chitosan/pyroligneous acid film (F1), chitosan/pyroligneous/minerals (F2) after spraying, for evaluation of vigor and development on beans (C) and potato (D)
Figure 9:
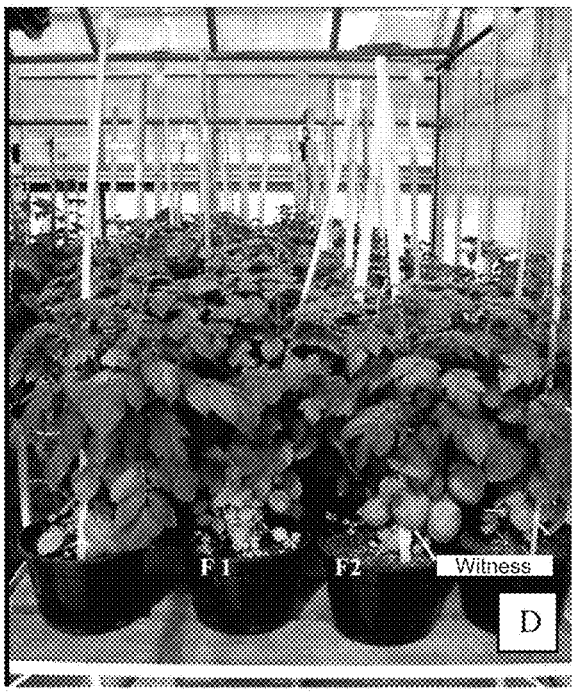

FIG. 9 shows the good development of the plants treated with formulations of the invention (DPE+chitosan) and (DPE+chitosan+minerals). The evaluation of the activity of the peroxidase (PO), phenylamineammonia-liase (FAL), β 1,3 GLUCANASE (β 1,3) after application of the formulations pyroligneous acid/chitosan and pyroligneous acid/chitosan/minerals, in cultivation of hybrid pepper cv. Mitla, inoculated with nematodes Meloidogyne is shown in Table 3 below.

TABLE 3

Activity of the peroxidase (PO), phenylamineammonia-liase (FAL), β 1,3 glucanase (β 1,3) after application of the formulations DPE/chitosan and DPE/chitosan/minerals, in cultivation of hybrid pepper cv. Mitla, inoculated with nematodes Meloidogyne

| DPE/chitosan | PO ue/min/g of tissue | FAL ue/min/g of tissue | β 1,3 ue/g of tissue | PFO ue/min/g of tissue |
|---|---|---|---|---|
| DPE/chitosan | 385.91 b | 28.41 ab | 39.68 b | 438.90 b |
| DPE/chitosan/nutrients | 320.00 c* | 32.29 a | 37.56 b | 426.67 b |
| Test. Inoculated with nematode | 472.58 a | 27.45 b | 62.86 a | 498.77 a |
| Test. Positive | 134.80 d | 29.98 ab | 29.26 c | 354.43 c |

*Different letters differ from each other in the columns by the Duncan test (p < 0.05).

Figure 10:
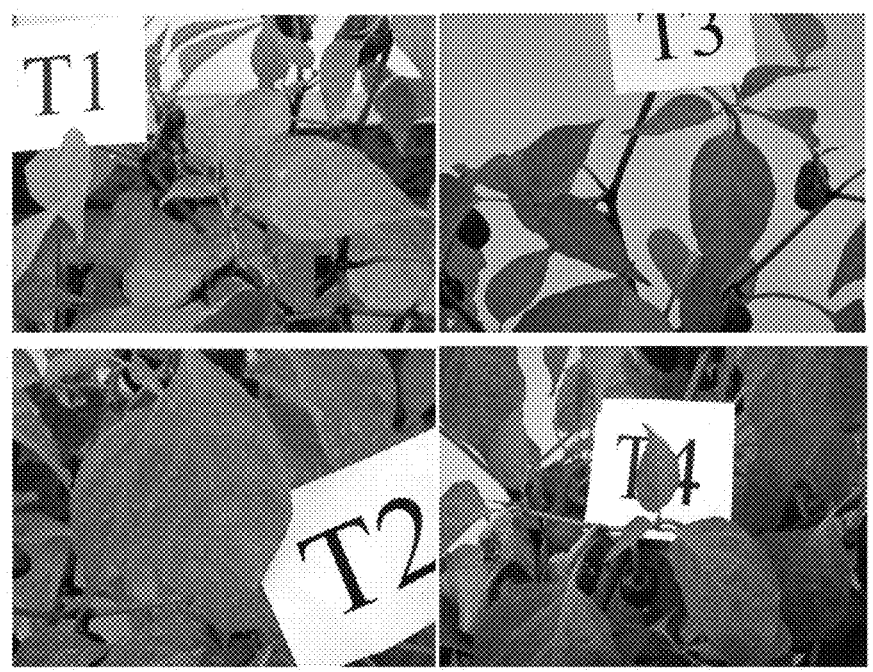
FIG. 10—Hybrid pepper plants cv. *Mitla* inoculated with nematodes and treated with the formulations pyroligneous extract/chitosan (T3) and pyroligneous extract/chitosan/minerals (T4), positive witness (T1), witness with nematodes (T2), showing the presence of necrosis on the leaves.
Figure 11:
FIG. 11—Difference in the vigor of hybrid pepper cv. Mitla plants inoculated with nematode and treated with the formulations pyroligneous extract/chitosan (T3) and pyroligneous extract/chitosan/minerals (T4), positive witness (T1), witness with nematode (T2)

In table 3, the activity of the proteins related to the pathogenesis (β 1,3 glucanase, PO, PFO and FAL) involved in defense responses and resistance to various types of environmental stress exhibited significant alterations, when the plants were treated with the formulation of the invention. This indicates that the formulation of the invention activated the defense metabolism at the moment when the plant was attacked in some way, promoting a rapid defense. In this case, one observed the presence of necrosis on the leaves of the witnesses (FIG. 10), indicating that the phytoprotection process did not take place on these untreated plants. This is confirmed by observing Table 4, where it is possible to observe that the phenolic compounds (polyphenols, monophenols, and ortho- and diphenols, etc.), which are substrates for the enzymes PO, PFO and FAL, were not synthetized by the plant in the absence of the formulation of the invention. One observed that, on the witness, there was a significant decrease in the concentration of these phenols. Thus, the plant, upon not managing to defend itself from the attacks, demanded a higher expenditure of energy by its organism and thereby caused the vigor and the production to be drastically reduced (FIG. 11 and Table 5). In this way, one concluded that the defense process was not activated and the plant became more susceptible. The phenolic compounds are tannins, which, when present in the leaves, participate in the lignification process and production of phytoalexines, and also make the plants more indigestible and/or less attractive to the phylophagous insects (insects that feed on leaves) and sucking insects, rendering these plants more resistant to these pests as well. From the results presented, one can conclude that the formulation of the invention exhibited the characteristic of the action of inducing systemic resistance of the plants.

TABLE 4

Evaluation of the contents of phenolic compounds (mg/100 g) extracted in methanol, 50% methanol and water after application of the formulations pyroligneous acid/chitosan and pyroligneous acid/chitosan/minerals, in cultivation of hybrid cv. Mitla pepper

| Phytoprotectors | 50% methanol mg/100 g | 100% methanol mg/100 g | water mg/100 g | Total phenolic compounds mg/100 g |
|---|---|---|---|---|
| Pyrolignoleus acid/chitosan | 2.21 a | 3.69 a | 1.18 a | 7.08 a |
| Pyroligneous/chitosan/micronutrients | 2.29 a | 3.72 a | 1.20 a | 7.21 a |
| Test. Inoculated with nematode | 1.86 b | 2.19 b | 1.18 a | 5.23 b |
| Test. Positive | 1.98 b | 2.42 b | 0.77 b | 5.17 b |

* Different letters differ from each other in the column by the Duncan test (p < 0.05).

TABLE 5

Evaluation of the vigor and production of hybrid cv. Mitla pepper after treatments with the formulations pyroligneous acid/chitosan and pyroligneous acid/chitosan/minerals in cultivation of hybrid cv. Mitla pepper.

| Formulations | Weight/plant g | Number of fruits per plant |
|---|---|---|
| Pyroligneous acid/chitosan | 131.00 b | 25.00 b |
| Pyroligneous acid/chitosan/nutrients | 158.33 a | 31.00 a |
| Test. Inoculated with nematodes | 126.00 b | 17.00 c |
| Test. Positive | 120.00 b | 12.00 c |

* Different letters differ from each other in the column by the Duncan test ($p < 0.05$).

Figure 12:
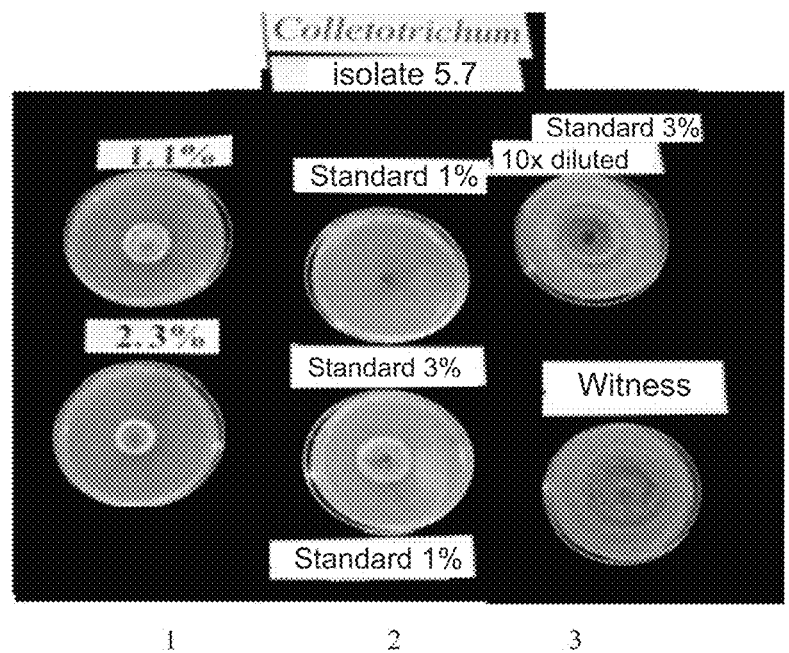
FIG. 12—Inhibition of the micellar growth of the isolate 5.7 *Colletotrichum gloeosporioides*, caused by the fertilizing phytoprotective formulation pyroligneous acid/chitosan, reference in the photo for 1.1% and 2.3%, (2) the standard fungicide used for controlling the fungus, (3) witness and 10× diluted standard fungicide.
Figure 13:
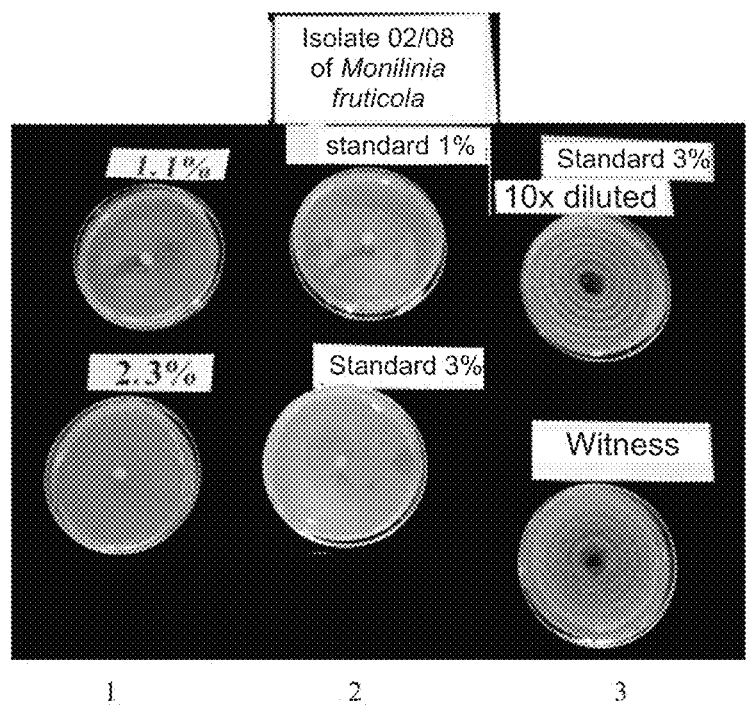
FIG. 13—Inhibition of the micellar growth of the isolate 02/08 of *Monilinia fruticola* by the phytoprotective formulation pyroligneous acid/chitosan, reference in the photo for 1.1 and 2.3% (1) and (2) the standard fungicidal used for controlling the fungus, (3) witness and 10× diluted standard fungicide.

FIGS. 12 and 13 show results of the inhibition of the micellar growth of isolates of *Colletotrichum* and *Monilinia* by using the formulation of the invention, proven the fungitoxic action of the formulation.

Experiments for evaluation of the effect of the formulation of the invention were also carried out with a view to test the resistance of diseases and quality of fruit on apple trees cv Fuji. The interest of an alternative product in this crop is the adaptation to international rules for the integrated production, reduction of agricultural defensives and of environmental attacks. The experiments were carried out by using three plants by repetition and three repetitions by treatment. One bordure plant was left between the repetitions and 108 plants were used in the experiment.

The first analysis was carried out in the experiment in conventional crops was for the contents of pectin in the fruits. The presence of pectin guarantees the juiciness of the fruit, when the pectinase acts by hydrolyzing the pectin. In a normal senescence process, apple exhibits flour-like texture, losing quality. So, it is ideal to keep the juiciness for as long as possible during storage. The results are shown in Table 6 below.

TABLE 6

Contents of pectin (µg/mg) in apple from an orchard treated with formulates pyroligneous extract/chitosan and pyroligneous extract/chitosan/minerals and witness with conventional treatment of the crop, during the period of storage of the fruits at average room temperature of 24 to 26° C. In order to accelerate the senescence process, the apples were stored at room temperature ranging from 24 to 26° C., for 120 days.

| Formulations | Pectin (µg/mg) 08/04 | Pectin (µg/mg) 27/04 | Pectin (µg/mg 18/05 | Pectin (µg/mg 23/06 |
|---|---|---|---|---|
| Formulation-T5 | 51.24 b | 48.93 bc | 41.72 a | 34.89 bcd |
| Pyroligneous extract/chitosan | 54.31 a | 52.17 a | 44.83 a | 36.43 abc |
| Pyroligneous extract/chitosan/ minerals | 58.99 a | 56.06 a | 39.69 a | 37.09 ab |
| Formulation 15-T9 | 50.60 b | 48.98 bc | 39.93 a | 38.00 a |
| Witness-T1 | 49.90 b | 46.04 c | 41.48 a | 33.24 d |
| Variation Coefficient (%) | 5.4 | 5.7 | 6.2 | 3.9 |

* Different letters differ from each other in the column by the Duncan test ($p < 0.05$).

The analysis of Table 6 shows that, even in conditions suitable for acceleration of senescence, the plants treated with the formulation of the invention exhibited, after 120 days' storage, higher contents of pectin in the fruit.

The invention claimed is:

1. A process for obtaining a thermally stable formulation with fertilizing and phytoprotective capability, comprising the following steps:
    A) Obtaining a distilled pyroligneous extract (DPE) by vacuum distillation of a crude pyroligneous extract (CPE) at a temperature of 60° C. to 75° C.;
    B) Obtaining a composition comprising the DPE and chitosan;
    C) Obtaining a fertilizing mineral solution;
    D) Mixing the composition obtained in step B with the solution obtained in step C.

2. The process for obtaining the thermally stable formulation with fertilizing and phytoprotective capability according to claim 1, wherein the composition of step B of the process is obtained by mixing the chitosan and the DPE.

3. The process for obtaining the thermally stable formulation with fertilizing and phytoprotective capability according to claim 2, wherein the chitosan has a minimum distillation degree of 97%.

4. The process for obtaining the thermally stable formulation with fertilizing and phytoprotective capability according to claim 2, wherein the concentration of the chitosan in the composition of step B ranges from 0.05 g/L to 30 g/L.

5. The process for obtaining the thermally stable formulation with fertilizing and phytoprotective capability according to claim 2, wherein conductivity of the composition obtained in step B ranges from 1038 µS cm$^{-1}$ to 4970 µS cm$^{-1}$.

6. The process for obtaining a thermally stable formulation with fertilizing and phytoprotective capability according to claim 2, wherein the composition obtained in step B has a concentration of the chitosan of 1 g/L.

7. The process for obtaining the thermally stable formulation with fertilizing and phytoprotective capability according to claim 2, wherein the composition obtained in step B has a conductivity ranging from 1938 µS cm$^{-1}$ to 2190 µS cm$^{-1}$.

8. The process for obtaining the thermally stable formulation with fertilizing and phytoprotective capability according to claim 1, wherein the solution in step C is obtained by adding minerals to water.

9. The process for obtaining the thermally stable formulation with fertilizing and phytoprotective capability according to claim 8, wherein the minerals are selected from silicon and/or boron and/or molybdenum and/or manganese and/or zinc and/or calcium and/or copper.

10. The process for obtaining the thermally stable formulation with fertilizing and phytoprotective capability according to claim 9, wherein concentrations of minerals in an aqueous solution are: silicon: 0.07 g/L to 0.5 g/L; boron: 0.04 g/L to 0.08 g/L; molybdenum: 0.02 g/L to 0.09 g/L; manganese: 0.04 g/L to 0.13 g/L; zinc: 0.02 g/L to 0.1 g/L; calcium; 0.03 g/L to 0.3 g/L; copper 0.065 g/L to 0.2 g/L.

11. The process for obtaining the thermally stable formulation with fertilizing and phytoprotective capability according to claim 1, wherein the mixing ratio between the solutions B:C ranges from 0.05:99.95 to 30:70.

12. A thermally stable formulation with fertilizing and phytoprotective capability, comprising distilled pyroligneous extract (DPE), chitosan and mineral solution prepared by a process of
    A) Obtaining a distilled pyroligneous extract (DPE) by vacuum distillation of a crude pyroligneous extract (CPE) at a temperature of 60° C. to 75° C.;
    B) Obtaining a composition comprising the DPE and chitosan;

C) Obtaining a fertilizing mineral solution;
D) Mixing the composition obtained in step B with the solution obtained in step C.

13. The thermally stable formulation with fertilizing and phytoprotective capability according to claim 12, wherein concentration of chitosan in the formulation ranges from $2.5 \times 10^{-5}$ g/L to 9 g/L.

14. The thermally stable formulation with fertilizing and phytoprotective capability according to claim 12, wherein the minerals in the formulation are selected from silicon and/or boron and/or molybdenum and/or manganese and/or zinc and/or calcium and/or copper.

15. The thermally stable formulation with fertilizing and phytoprotective capability according to claim 14, wherein concentrations of the minerals are: silicon: 0.049 g/L to 0.5 g/L; boron: 0.028 g/L to 0.08 g/L; molybdenum: 0.014 g/L to 0.09 g/L; manganese: 0.028 g/L to 0.13 g/L; zinc: 0.014 g/L to 0.1 g/L; calcium; 0.021 g/L to 0.3 g/L; copper 0.046 g/L to 0.2 g/L.

16. A process comprising applying the thermally stable formulation with fertilizing and phytoprotective capability according to claim 12 to plants.

17. A process comprising forming a film of the thermally stable formulation with fertilizing and phytoprotective capability according to claim 12 on a plant.

* * * * *